(12) United States Patent
Lim et al.

(10) Patent No.: US 9,046,489 B2
(45) Date of Patent: Jun. 2, 2015

(54) FLUORESCENCE IMAGING DEVICE

(71) Applicant: Logos Biosystems, Inc., Anyang-si (KR)

(72) Inventors: Hyun Chang Lim, Seoul (KR); Neon Cheol Jung, Anyang-si (KR); Keun Chang Cho, Seoul (KR)

(73) Assignee: LOGOS BIOSYSTEMS, INC. (KR)

( * ) Notice: Subject to any disclaimer, the term of this patent is extended or adjusted under 35 U.S.C. 154(b) by 0 days.

(21) Appl. No.: 14/224,442

(22) Filed: Mar. 25, 2014

(65) Prior Publication Data
US 2014/0291547 A1    Oct. 2, 2014

(30) Foreign Application Priority Data
Mar. 27, 2013 (KR) .................. 10-2013-0032808

(51) Int. Cl.
G01N 21/64 (2006.01)
G02B 21/16 (2006.01)

(52) U.S. Cl.
CPC ............ *G01N 21/6458* (2013.01); *G02B 21/16* (2013.01)

(58) Field of Classification Search
CPC .......................... G01N 21/6458; G02B 21/16
USPC ...................................................... 250/458.1
See application file for complete search history.

(56) References Cited

U.S. PATENT DOCUMENTS

| | | | |
|---|---|---|---|
| 5,905,268 A * | 5/1999 | Garcia et al. | 250/504 R |
| 6,582,363 B2 * | 6/2003 | Adachi et al. | 600/178 |
| 7,070,739 B1 * | 7/2006 | Anderson et al. | 422/82.05 |
| 8,000,003 B2 * | 8/2011 | Fey | 359/368 |
| 2002/0022766 A1 * | 2/2002 | Adachi | 600/160 |
| 2002/0026099 A1 * | 2/2002 | Adachi et al. | 600/178 |
| 2003/0081209 A1 * | 5/2003 | Takahashi et al. | 356/338 |
| 2003/0082516 A1 * | 5/2003 | Straus | 435/4 |
| 2003/0117628 A1 * | 6/2003 | Harju et al. | 356/417 |
| 2004/0120034 A1 * | 6/2004 | Miyawaki et al. | 359/385 |
| 2005/0110999 A1 * | 5/2005 | Erdogan et al. | 356/417 |
| 2005/0191705 A1 | 9/2005 | Werner et al. | |
| 2006/0166355 A1 * | 7/2006 | Gutekunst | 435/288.7 |
| 2007/0070350 A1 * | 3/2007 | Sugiyama et al. | 356/432 |
| 2009/0225410 A1 * | 9/2009 | Fey | 359/385 |
| 2010/0067102 A1 * | 3/2010 | Yokoi et al. | 359/385 |
| 2011/0188717 A1 * | 8/2011 | Baudry et al. | 382/128 |
| 2013/0201322 A1 * | 8/2013 | Park et al. | 348/80 |
| 2014/0218623 A1 * | 8/2014 | Kimura et al. | 348/744 |

FOREIGN PATENT DOCUMENTS

| | | |
|---|---|---|
| JP | 2008164841 | 7/2008 |
| KR | 1020120024436 | 3/2012 |
| WO | 9522058 | 8/1995 |

OTHER PUBLICATIONS

Korean Notice of Allowance—Korean Application No. 10-2013-0032808 issued on May 30, 2014.

* cited by examiner

*Primary Examiner* — Kiho Kim
(74) *Attorney, Agent, or Firm* — Cantor Colburn LLP

(57) ABSTRACT

An excitation light from a first light source is adapted to be irradiated to a subject without passing through an objective lens so that the first light source and the subject may be arranged to be adjacent to each other. As a result, an excitation light having a high intensity of radiation may be irradiated to the subject to obtain a strong fluorescence signal. In addition, since the optical path of the excitation light from the first light source and the optical path of the fluorescent emission light emitted from the first dichroic mirror and the white light do not coincide with each other, a high S/N ratio may be obtained.

9 Claims, 7 Drawing Sheets

FLUORESCENCE IMAGING DEVICE

BACKGROUND OF THE INVENTION

1. Field of the Invention

The present invention relates to a fluorescence imaging device, and more particularly, to a imaging device based on a fluorescence microscope optical system. More particularly, the present invention relates to a fluorescence imaging device configured to be capable of observing fluorescent images of subjects dyed with different fluorophores, which has a simple structure and is capable of being operated easily.

2. Description of the Prior Art

When ultraviolet rays and visible rays with a short wavelength are irradiated to a specimen, dye molecules of the specimen emit a light. A microscope used for observing a fluorescence of a visible ray range which is emitted at that time is referred to as a fluorescence microscope.

The specimen of the fluorescence microscope should have an element that develops a fluorescence by itself or emits a fluorescence when it absorbs a short wavelength. For this purpose, the specimen is processed by a fluorophore (a fluorescent dye) and a light, of which a wavelength is absorbed to the fluorophore, is irradiated to the specimen so as to observe the specimen through a radiation light emitted from the specimen.

The fluorescence microscope may easily sense a very small amount of a fluorophore. Thus, the fluorescence microscope is used when studying a distribution or a moving path of a fluorophore existing in a specimen, a cell, etc. which may not be identified by a human.

In addition, such a fluorescence microscope has been used for various types of imaging devices which may automatically analyze a feature of a nucleic acid, an intracellular material, or a cell itself. For example, an automatic cell counter has been frequently used in a state where a bright-field optical system is incorporated therein. When a specimen containing a cell to be measured is not purely separated, the bright-field optical system cannot provide a correctly measured value. In order to overcome this problem, automated fluorescence cell counters have been developed which measure a fluorescence dyed specimen using a fluorescence microscope method. In addition, an equipment such as a DNA sequencer, a DNA chip scanner, or an image cytometry is also configured to basically incorporate a fluorescence microscope optical system and to connect the fluorescence microscope system with a proper driving unit and software so as to acquire and analyze a fluorescence image.

The configurations and functional actions of conventional fluorescence microscopes are as follows.

A conventional fluorescence microscope selects a monochromatic light which coincides with an absorption wavelength of a fluorescent body in a white light through an excitation filter, adjusts the path of the monochromatic light of the selected absorption wavelength using a dichroic mirror so as to irradiate the monochromatic light to the specimen through an objective lens, selects a light which coincides with a color development wavelength of the fluorescent body of the specimen in the light produced by the fluorescent body of the specimen and transmitted by the objective lens and the dichroic mirror, using an emission filter, and provides the selected light to an image sensor.

The image sensor is implemented by an imaging element such as an eyepiece or a Charge Coupled Device (CCD) and detects and presents a color development wavelength of the fluorescent body attached to the specimen so that the shape of the specimen can be observed.

Recently, fluorescence microscopes of a type configured to irradiate various lights to a specimen to obtain fluorescent images and then compare the fluorescent images with each other so as to observe a correct shape of the specimen, rather than being configured to obtain a single fluorescent image according to a light irradiated to a specimen, are being developed. Schematic configurations of such fluorescence microscopes are illustrated in FIGS. 1 and 2.

The fluorescence microscope illustrated in FIG. 1 is adapted to use a separate light source for each wavelength and to execute an observation while changing individual filter assemblies 100 (including a light sources 101, a focusing lens 102, an excitation filter 103, a dichroic mirror 104, and an emission filter 105) as desired.

However, the fluorescence microscope illustrated in FIG. 1 has a problem in that, since the light source 101 is irradiated via an objective lens 107, a subject S is distant from the light source 101 and thus, the intensity of radiation is weak so that the intensity of an observed fluorescence signal is weakened.

The fluorescence microscope of this type should be provided with individual filter assemblies 100. Thus, the fluorescence microscope has a complicated configuration and a large volume, which inevitably increases the manufacturing costs.

The fluorescence microscope illustrated in FIG. 2 is configured to be provided with one light source 101 configured to irradiate excitation light and one excitation filter 102 to detect lights of various wavelengths using a plurality of dichroic mirrors 104 and image sensors 106.

The fluorescence microscope of the type illustrated in FIG. 2 has a stable structure since it is not required to move a filter assembly unlike the fluorescence microscope illustrated in FIG. 1. However, the fluorescence microscope illustrated in FIG. 2 also has a problem in that, since the light source 101 irradiates the subject S via the objective lens 107, the intensity of radiation is weak and thus, the intensity of a fluorescence signal is weakened. In addition, since it is necessary to use a plurality of dichroic mirrors 104 and expensive image sensors 106, the manufacturing costs are also increased.

Further, the fluorescence microscopes illustrated in FIGS. 1 and 2 are provided with dichroic mirrors 104 between an objective lens 107 and an image sensor 106 and, when observing a bright-field image, the dichroic mirrors 104 should be removed. However, the light path when the dichroic mirrors 104 are present and the light path when the dichroic mirrors 104 are absent become different from each other due to the refraction of light, and a bright-field image and a fluorescence image become substantially different from each other without being overlapped. Consequently, there is a problem in that it is difficult to compare the two images.

In order to solve this problem, an infinity-corrected objective lens is used instead of a finite conjugate objective lens. In such a case, there is a problem in that, since a tube lens having a predetermined focal length is additionally required, more space is required and the size of the equipment is increased.

SUMMARY OF THE INVENTION

An object of the present invention is to provide a fluorescence imaging device which is capable of irradiating a high intensity of radiation by positioning a fluorescence light source on an on-axis between an objective lens and a subject, excluding a variation in light path according to the refraction of light at the time of observing a fluorescence image and a bright-field image, and obtaining a high S/N ratio from the fluorescence image since the light of the light source is not directed to the objective lens or an image sensor so as to lower a background level.

Another object of the present invention is to provide a fluorescence imaging device capable of observing subjects dyed with different fluorophores, which has a simple structure and is capable of being stably operated and suppressing occurrence of a focus shift.

In order to achieve the above described objects, there is provided a fluorescence imaging device including: a first light source which is a fluorescence light source; a second light source configured to irradiate a white light or a monochromatic light to a subject; an excitation filter configured to selectively transmit an excitation light irradiated by the first light source; a first dichroic mirror configured to transmit an excitation light transmitted by the excitation filter, to the subject and to reflect a fluorescent emission light emitted from the subject and a second light from the second light source; an objective lens configured to concentrate the fluorescent emission light reflected by the first dichroic mirror and the second light; an emission filter configured to transmit a light of a predetermined wavelength in the fluorescent emission light concentrated by the objective lens; and a detector configured to sense an image from the light that has been transmitted through the emission filter and the second light.

In addition, there is provided a fluorescence imaging device including: a first light source which is a fluorescence light source; a second light source configured to irradiate a white light or a monochromatic light to a subject; an excitation filter configured to selectively transmit an excitation light irradiated by the first light source; a second dichroic mirror configured to reflect an excitation light transmitted by the excitation filter, to the subject and to transmit a fluorescent emission light emitted from the subject and a second light from the second light source; an objective lens configured to concentrate the fluorescent emission light transmitted by the second dichroic mirror and the second light; an emission filter configured to transmit a light of a predetermined wavelength in the fluorescent emission light concentrated by the objective lens; and a detector configured to sense an image from the light transmitted by the emission filter and the second light.

Further, there is provided a fluorescence imaging device including: a first light source which is a fluorescence light source; an excitation filter configured to selectively transmit an excitation light irradiated by the first light source; a first dichroic mirror positioned between an objective lens and a subject, the first dichroic mirror being configured to transmit an excitation light transmitted by the excitation filter to the subject and to reflect a fluorescent emission light emitted from the subject; the objective lens configured to concentrate the fluorescent emission light reflected by the first dichroic mirror; an emission filter configured to transmit a light of a predetermined wavelength in the fluorescent emission light concentrated by the objective lens; and a detector configured to sense an image from the fluorescent emission light transmitted by the emission filter.

Moreover, there is provided a fluorescence imaging device including: a first light source which is a fluorescence light source; an excitation filter configured to selectively transmit an excitation light irradiated by the first light source; a second dichroic mirror positioned between an objective lens and a subject, the first dichroic mirror being configured to reflect an excitation light transmitted by the excitation filter to the subject and to transmit a fluorescent emission light emitted from the subject; the objective lens configured to concentrate the fluorescent emission light transmitted by the second dichroic mirror; an emission filter configured to transmit a light of a predetermined wavelength in the fluorescent emission light concentrated by the objective lens; and a detector configured to sense an image from the fluorescent emission light transmitted by the emission filter.

Here, a plurality of first light sources, excitation filters, first dichroic mirrors, and second dichroic mirrors may be provided to be classified according to wavelengths.

In addition, a plurality of emission filters may be provided so as to transmit wavelengths of different regions, respectively, and selectively arranged on a path of the fluorescent emission light.

The plurality of emission filters may have different thicknesses.

In the fluorescence imaging device, the plurality of emission filters may be positioned and moved on the same plane.

The fluorescence imaging device may further include a filter wheel to which the plurality of emission filters are coupled. The filter wheel arranges each of the emission filters on the path of the fluorescent emission light while rotating about a rotation shaft.

The fluorescence imaging device may further include a drive motor and a driving gear rotated by the drive motor. A gear is formed on the rim of the filter wheel and the filter wheel is engaged with the driving gear directly or indirectly to be rotated with the driving gear.

In the fluorescence microscope of the present invention, a plane formed by the plurality of emission filters is orthogonal to the path of the fluorescent emission light.

In addition, a combination may be made such that the center wavelength of the light transmitted by the excitation filter is 360 nm, the reference wavelength of the light transmitted by the first dichroic mirror or the reference wavelength reflected by the second dichroic mirror is 400 nm, and the emission filters transmit wavelengths of 450 nm and 530 nm.

Otherwise, a combination may be made such that the center wavelength of the light transmitted by the excitation filter 30 is 475 nm, the reference wavelength of the light transmitted by the first dichroic mirror 40 or the reference wavelength of the light reflected by the second dichroic mirror 41 is 500 nm, and the emission filters 60 transmits the wavelengths of 530 nm and 600 nm.

Otherwise, a combination may be made such that the center wavelength of the light transmitted by the excitation filter 30 is 525 nm, the reference wavelength of the light transmitted by the first dichroic mirror 40 or the reference wavelength of the light reflected by the second dichroic mirror 41 is 560 nm, and the emission filters 60 transmit the wavelengths of 595 nm and 690 nm.

According to the present invention, an excitation light from a first light source is adapted to be irradiated to a subject without passing through an objective lens so that the first light source and the subject may be arranged to be adjacent to each other. As a result, an excitation light having a high intensity of radiation may be irradiated to the subject to obtain a strong fluorescence signal. In addition, since the fluorescent emission light emitted from the first dichroic mirror and the second light (a white light or a monochromatic light) from the second light source are adapted to be reflected by the first dichroic mirror, a fluorescence image and a bright-field image may be observed without removing the first dichroic mirror. As a result, a change in optical path according to a refraction of light may be excluded and thus, the fluorescence image and the bright-field image may be easily compared with each other.

In addition, even though only one light source, only one focusing lens, only one excitation filter, and only one dichroic mirror are used, different images may be acquired through a plurality of emission filters. In addition, the structure is simple and the manufacturing costs may be reduced.

Further, subjects dyed with different fluorophores may be observed by moving only the emission filters without moving the whole of a filter assembly (including the light source, the focusing lens, the excitation filter, the dichroic mirror, and the emission filters) unlike the conventional fluorescence imaging device. Thus, the size and load of a moving part may be reduced and a change in alignment state of an optical path may be minimized.

In addition, when the thicknesses of the emission filters are set to be different from each other and arranged to be suitable for wavelengths of the transmitted fluorescent emission lights, it is possible to minimize a change of focus of the fluorescent emission light while the fluorescent emission light passes through the dichroic mirror and the emission filter.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE EXEMPLARY EMBODIMENTS

Hereinafter, various embodiments of the present invention will be described in detail with reference to the accompanying drawings. For the purposes of clarity and simplicity, a detailed description of known functions and configurations incorporated herein will be omitted as it may make the subject matter of the present invention rather unclear.

Figure 1:
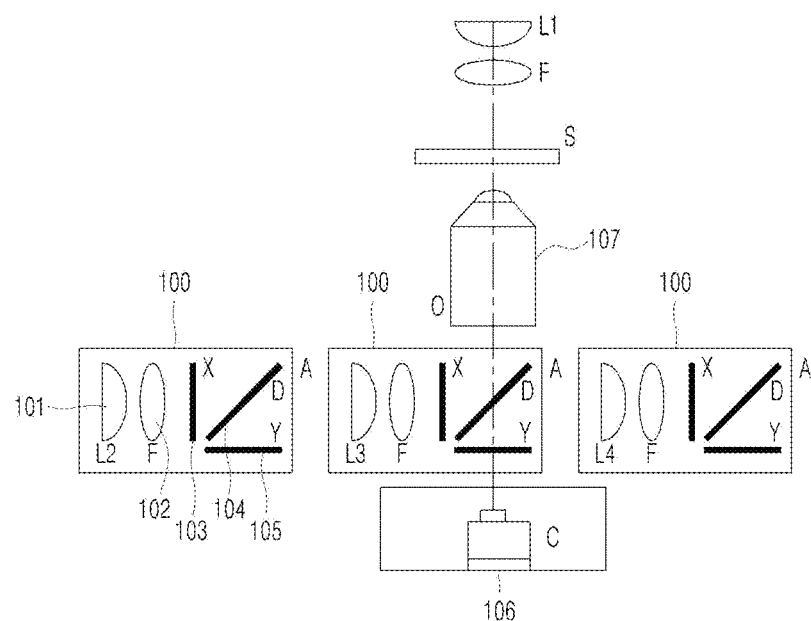
FIGS. 1 and 2 are views illustrating schematic configurations of conventional fluorescence microscopes.
Figure 2:
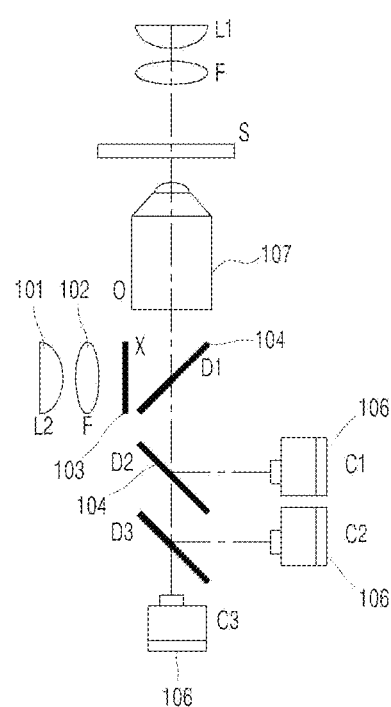
Figure 3:
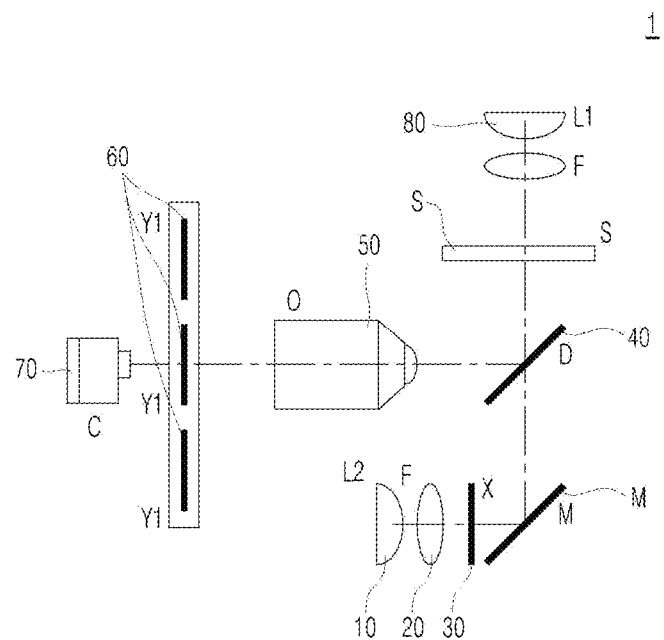
FIG. 3 is a view illustrating a schematic configuration of a fluorescence imaging device according to an exemplary embodiment of the present invention.

FIG. 3 is a view illustrating a schematic configuration of a fluorescence imaging device 1 according to an exemplary embodiment of the present invention.

The fluorescence imaging device 1 according to the present invention refers to an imaging device based on a fluorescence microscope optical system. Therefore, equipment such as an automated cell counter, an automated fluorescence cell counter, a DNA sequencer, a DNA chip scanner, and an image cytometry as well as a conventional fluorescence microscope may be included in the fluorescence imaging device 1 of the present invention.

The fluorescence imaging device 1 according to the exemplary embodiment of the present invention may include a first light source 10, an excitation filter 30, a first dichroic mirror 40, an objective lens 50, an emission filter 60, and a detector 70. Further, the fluorescence imaging device 1 may further include a second light source 80.

The first light source 10 is a fluorescence light source and may be configured by, for example, a UV LED, a blue LED, a green LED, a yellow LED, an orange LED, or a red LED so as to supply an excitation light having a needed wavelength. The first light source 10 configured by a Light Emitting Diode (LED) has a long life, allows a stable observation of a subject S since the rate of degradation of an intensity of radiation is small as compared to a mercury lamp, is capable of preventing a thermal deformation phenomenon since the heat generation is low, and may contribute to the reduction of the size of the fluorescence imaging device 1 since the size of the LED itself is small.

A first light in the present invention is a light irradiated from the first light source 10 and is differentiated from a second light. The first light radiated from the first light source 10 is transferred to the excitation filter 30 via a focusing lens 20.

The excitation filter 30 selectively transmits an excitation light irradiated by the first light source 10.

As illustrated in FIG. 3, the first light source 10, the focusing lens 20, and the excitation filter 30 may be arranged such that an excitation light may be reflected by a reflector M or arranged in a direction directed toward the subject S (in the vertical direction on the drawing) without the reflector M.

A second light source 80 is formed at the subject S side (the opposite side to the first light source) on the extension of the path of the excitation light and configured to irradiate a white light or a monochromatic light to the subject S. In the present invention, the second light is a light irradiated by the second light source 80 and may be configured by the white light or the monochromatic light (light having a short wavelength). The second light irradiated to the subject S is transferred to the detector 70 via the first dichroic mirror 40 and the emission filter 60 or a glass window, and allows the detector 70 to acquire a bright-field image.

The first dichroic mirror 40 transmits the excitation light transmitted by the excitation filter 30, toward the subject S and reflects the fluorescent emission light emitted from the subject S and the second light from the second light source.

In general, a dichroic mirror may be configured to reflect a light of a specific wavelength and transmit lights of other wavelengths. For example, the dichroic mirror may be configured to reflect a light having a short wavelength and to transmit a light having a long wavelength. On the contrary, the dichroic mirror may be configured to transmit the short wavelength and reflect the long wavelength.

In the present invention, the first dichroic mirror 40 is configured to transmit a light having a short wavelength and to reflect a light having a long wavelength. That is, the first dichroic mirror 40 transmits the excitation light transmitted by the excitation filter 30, toward the subject S and reflects the fluorescent emission light emitted from the subject S and the second light from second light source to be transferred to the emission filter 60 and the detector 70. The first dichroic mirror 40 is positioned between the objective lens 50 and the subject S.

In addition, a plurality of first light sources 10, excitation filters 30, and first dichroic mirrors 40 may be provided which are classified according to wavelengths. That is, similarly to the type illustrated in FIG. 4, when a plurality of first dichroic mirrors 40 are provided and reference wavelengths respectively transmitted by the plurality of first dichroic mirrors 40 are made to be different from each other, excitation lights of sequential wavelength ranges may be transferred from the plurality of first light sources 10 to subjects S, respectively.

The objective lens 50 concentrates the fluorescent emission lights and the second lights reflected by the first dichroic mirrors 40 and transfers the concentrated lights to the subjects S.

In the fluorescence imaging device 1 according to the present invention, the subjects S, i.e. specimens are processed by a specific reagent. The excitation lights transferred to the subjects S cause the energy of the specimens to be excited to excited states and the specimens are returned to the stable states while emitting the absorbed energies again. At this time, fluorescent lights are emitted.

The lights emitted again will have wavelengths somewhat inclined to the red direction. For example, when blue rays are absorbed, green rays are emitted from the subject S and green rays are converted into an orange light. The orange color is converted into a reddish orange color, and UV rays which are invisible to the naked eye are converted into visible rays. Such changes are referred to as a Stokes shift.

Due to such a Stokes shift, a fluorescent emission light has a somewhat longer wavelength as compared to an excitation light, and when transmitted by the first dichroic mirrors 40, the excitation light is transmitted and the fluorescent emission light is reflected.

The fluorescent emission lights emitted from the subjects S are reflected by the first dichroic mirrors 40, transmitted by the objective lens 50, and transmitted by the emission filters 60.

The emission filters 60 remove optical noise from the fluorescent emission lights emitted from the subjects S and select and transfer only the fluorescent emission lights with a desired wavelength to the detector 70.

In the fluorescence imaging device 1 according to the present invention, a detector 70 is configured to visually implement an image of a subject S (specimen) based on a fluorescent emission lights transmitted by an emission filter 60. For this purpose, the detector 70 may include a Charge Coupled Device (CCD) or a Complementary Metal-Oxide Semiconductor (CMOS).

As described above, in the fluorescence imaging device 1 according to the present invention, the excitation light of the first light source 10 is not irradiated to the subject S via the objective lens 50, and a light having a high intensity of radiation may be irradiated by positioning the first light source 10 on the on-axis between the objective lens and the subject S so as to reduce the distance from the first light source 10 to the subject S. As a result, a clear image based on a strong fluorescence signal may be obtained.

In addition, the first light source 10 is arranged below the subject S rather than above the subject S and thus, does not coincide with the optical path of the fluorescent emission light reflected by the first dichroic mirror 40 and transferred to the objective lens 50 and the detector 70. Therefore, the background level is lowered so that a high S/N ratio can be obtained from the fluorescence image.

Figure 4:
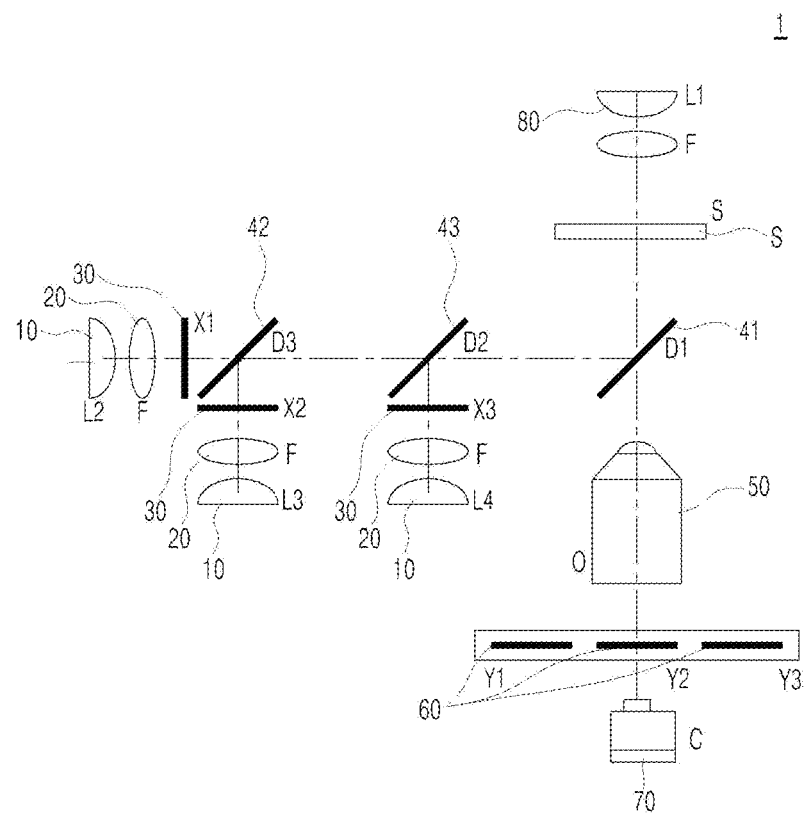
FIG. 4 is a view illustrating a schematic configuration of a fluorescence imaging device according to another exemplary embodiment of the present invention.
Figure 5:
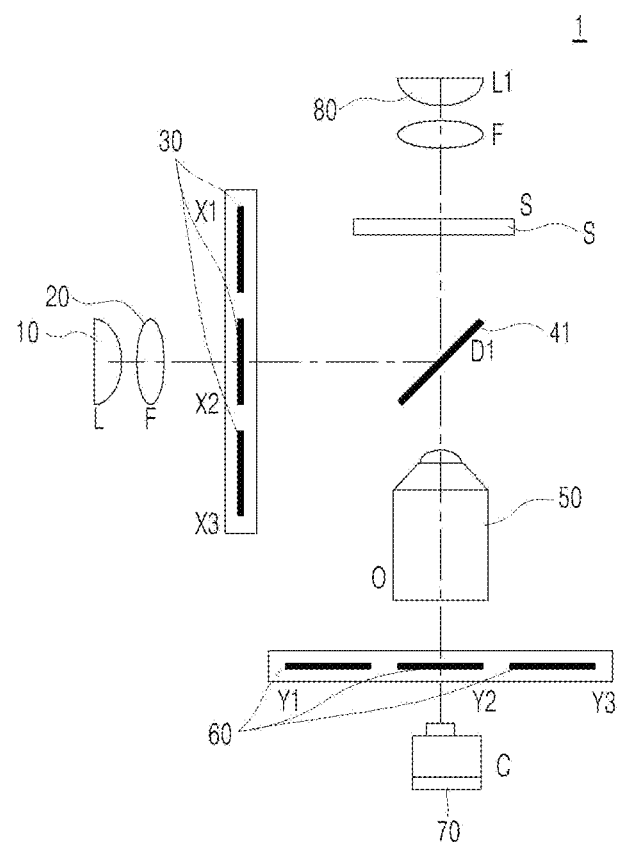
FIG. 5 is a view illustrating a schematic configuration of a fluorescence imaging device according to still another exemplary embodiment of the present invention.

FIG. 4 illustrates a schematic configuration of a fluorescence imaging device 1 according to another exemplary embodiment, and FIG. 5 illustrates a schematic configuration of a fluorescence imaging device 1 according to still another exemplary embodiment.

The fluorescence imaging device 1 according to an exemplary embodiment may include a first light source 10, an excitation filter 30, a second dichroic mirror 41, an objective lens 50, an emission filter 60, and a detector 70. In addition, the fluorescence imaging device 1 may further include a second light source 80.

In addition, a plurality of first light sources 10, excitation filters 30, and second dichroic mirrors 41, 42 and 43 may be provided to be classified according to wavelengths.

As described above, a dichroic mirror may be configured to reflect a light of a specific wavelength and transmit lights with other wavelengths. In the present invention, the second dichroic mirror 41 is configured to reflect a light having a short wavelength and transmit a light having a long wavelength. That is, the second dichroic mirror 41 reflects an excitation light transmitted by the excitation filters 30, to the subject S and transmit a fluorescent emission light emitted from the subject S and a second light from the second light source to be transferred to the emission filters 60 and the detector 70. The second dichroic mirror 41 is positioned between the objective lens 50 and the subject S.

In addition, as illustrated in FIG. 4, when the second dichroic mirrors 42 and 43 are further provided in addition to the second dichroic mirror 41, the second dichroic mirrors 41, 42 and 43 may be configured such that a reference wavelength reflected by the second dichroic mirror 42 is shorter than a reference wavelength reflected by the second dichroic mirror 41, a reference wavelength reflected by the second dichroic mirror 43 is shorter than the reference wavelength reflected by the second dichroic mirror 42. As a result, the excitation lights of sequential wavelength ranges may be transferred from the first light sources 10 to the subject S, respectively.

Figure 6:
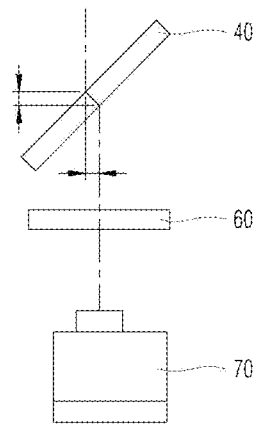
FIG. 6 is a view illustrating a focus shift occurring in a fluorescence microscope.
Figure 7:
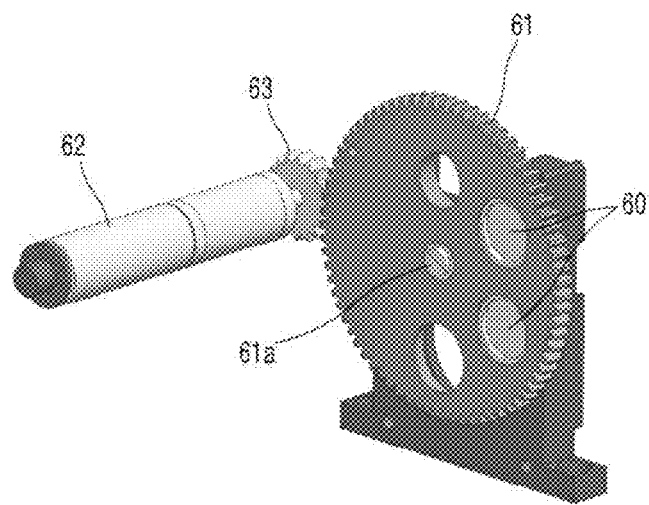
FIG. 7 is a perspective view illustrating some components of a fluorescence imaging device according to yet another exemplary embodiment of the present invention.
Figure 8A:
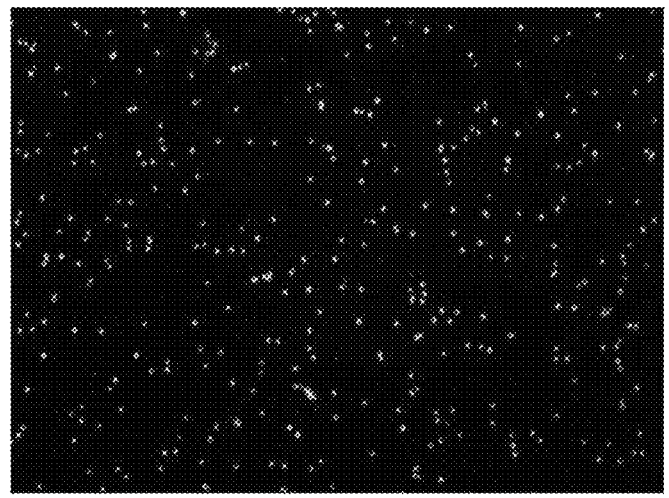
FIGS. 8A and 8B are photographs representing images observed by a fluorescence imaging device according to the present invention.
Figure 8B:
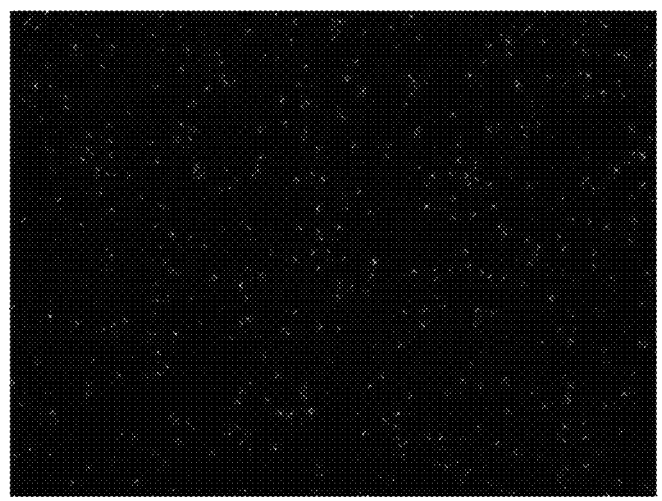

FIG. 6 is a view illustrating a focus shift occurring in a fluorescence microscope, FIG. 7 is a perspective view illustrating some components of a fluorescence imaging device 1 according to still another exemplary embodiment of the present invention, and FIGS. 8A and 8B are photographs representing images observed by the fluorescence imaging device 1 according to the present invention.

In the fluorescence imaging device 1 according to the present invention, two or more emission filters 60 are provided to transmit wavelengths of different regions. That is, the emission filters 60 are configured to transmit lights of which the wavelengths are different from each other such that the emission filters 60 may be suitable for fluorescent emission lights emitted from specimens which are dyed with different fluorophores, respectively.

In addition, the emission filters 60 are selectively arranged on the paths of the fluorescent emission lights.

In addition, when two or more emission filters 60 are provided, the emission filters 60 may be configured to have different thicknesses so as to correct a focus shift which may occur when the emission filters 60 transmit wavelength of different regions, respectively.

As illustrated in FIG. 6, a light transmitted by the dichroic mirror 40 from the fluorescence microscope suffers from a change in longitudinal direction and thus, also generation a change of a focus. In order to solve the problem of changing the focus, an automatic focusing device that automatically adjusts a focus is used but is very expensive. In addition, although a user may adjust the positions of respective filters for focusing, there is a problem in that such an operation may diffuse a whole filter alignment state and the operation is troublesome.

In the present invention, the emission filters 60 are configured to have different thicknesses according to wavelengths in order to solve such problems.

A light having a smaller refractive index has a long wavelength and the refractive index is increased as the wavelength is reduced. Thus, a fluorescent emission light having a relatively short wavelength suffers from a large refraction when transmitted by the second dichroic mirror 41 and a fluorescent emission light having a relatively long wavelength suffers from a small refraction when transmitted by the second dichroic mirror 41.

As a result, when a light having a relatively short wavelength is transmitted by the second dichroic mirror 41, the path of the light is largely changed. Therefore, when the thicknesses of the emission filters 60 are adjusted according to the wavelengths, respectively, the change of the path of light may be compensated for.

In addition, the fluorescence imaging device 1 according to the present invention is configured such that only the emission filters 60 are movable without moving the first light source 10, the excitation filter 30, the first dichroic mirror 40, the second dichroic mirror 41, and the objective lens 50. The plurality of emission filters 60 are selectively arranged on the path of the fluorescent emission light emitted from the subject S to the emission filters 60.

For this purpose, the fluorescence imaging device 1 according to the present invention further includes a filter wheel 61 where the emission filters 60 are coupled, a drive motor 62 that rotates the filter wheel 61 and a driving gear 63.

The filter wheel 61 is formed in a disc shape and formed with a plurality of openings in a circumferential direction. The emission filters 60 are coupled to the openings, respectively. A rotation shaft 61a is formed at the center of the filter wheel 61, and the filter wheel 61 is configured to rotate about the rotation shaft 61a. When the filter wheel 61 rotates, each of the emission filters 60 is arranged on the path of the fluorescent emission light. Preferably, three or less emission filters 60 are provided so as to avoid a situation where wavelengths are overlapped on each other or a signal is too weak to detect. In addition, a gear may be formed on the rim of the filter wheel 61 in the circumferential direction.

The drive motor 62 is provided at a side of the filter wheel 61, and is configured to be driven according to a control signal when it is required to replace the emission filters 60. The driving gear 63 is rotated by the drive motor 62 and engaged with the filter wheel 61 directly or indirectly so as to rotate the filter wheel 61 while being rotated.

Alternatively, the drive motor 62 may be connected with the filter wheel 61 through a belt or the like, and may be directly connected to the rotation shaft of the filter wheel 61.

The respective emission filters 60 coupled to the filter wheel 61 are positioned and moved on the same plane, and the plane formed by the emission filters 60 is orthogonal to the path of the fluorescent emission light.

As a result, the size and load of the moving part can be reduced because the subjects S dyed with different fluorophores may be observed only by moving the emission filters 60 by the filter wheel 61 rather than moving the whole of the filter assembly (including the light source, the focusing lens, the excitation filter, the dichroic mirror and the emission filters) unlike the conventional fluorescence imaging device, and the alignment state of the optical path can be stably maintained because the emission filters 60 may be stably replaced without changing the optical path.

In the fluorescence imaging device 1 according to an exemplary embodiment, a combination may be made such that the center wavelength of the light transmitted by the excitation filter 30 is 360 nm, the reference wavelength of the light transmitted by the first dichroic mirror 40 or the reference wavelength reflected by the second dichroic mirror 41 is 400 nm, and the emission filters 60 transmit wavelengths of 450 nm and 530 nm. The emission filter 60 that transmits the wavelength of 450 nm and the emission filter 60 that transmits the wavelength of 530 nm may have different thicknesses.

That is, two emission filters 60 may be provided so as to transmit the wavelengths of 450 nm and 530 nm. In this case, the first light source 10 may be made of a UV LED, the subject S sensed by the 450 nm emission filter 60 may be dyed with DAPI, and the subject S sensed by the 530 nm emission filter 60 may be dyed with GFP or acridine orange.

As a result, the excitation light transmitted by the excitation filter 30 has a short wavelength with reference to the first dichroic mirror 40 to be transmitted by the first dichroic mirror 40 or has a short wavelength with reference to the second dichroic mirror 41 to be reflected by the second dichroic mirror 41. The fluorescent emission light emitted after being irradiated to a subject S has a different wavelength according to a fluorescent substance and is converted into a long wavelength and sensed by the detector 70 after being transmitted by each of the emission filters 60.

In addition, in the fluorescence imaging device 1 of the present invention, a combination may be made such that the center wavelength of the light transmitted by the excitation filter 30 is 475 nm, the reference wavelength of the light transmitted by the first dichroic mirror 40 or the reference wavelength of the light reflected by the second dichroic mirror 41 is 500 nm, and the emission filters 60 transmits the wavelengths of 530 nm and 600 nm.

That is, two emission filters 60 may be provided to transmit the wavelengths of 530 nm and 600 nm. In this case, the first light source 10 may be made of a blue LED, the subject S sensed by the 530 nm emission filter 60 may be dyed with GFP or acridine orange, and the subject S sensed by the 600 nm emission filter 60 may be dyed with ethidium bromide or propidium iodide.

FIGS. 8A and 8B correspond to images acquired according to this exemplary embodiment, in which FIG. 8A is the case where the subject S is dyed with acridine orange and the 530 nm emission filter 60 is used and FIG. 8A is the case where the subject S is dyed with propidium iodide and the 600 nm emission filter 60 is used.

In addition, in the fluorescence imaging device 1 according to another exemplary embodiment of the present invention, a combination may be made such that the center wavelength of the light transmitted by the excitation filter 30 is 525 nm, the reference wavelength of the light transmitted by the first dichroic mirror 40 or the reference wavelength of the light reflected by the second dichroic mirror 41 is 560 nm, and the emission filters 60 transmit the wavelengths of 595 nm and 690 nm.

That is, two emission filters 60 may be provided to transmit the wavelengths of 595 nm and 690 nm. In this case, the first light source 10 may be made of a green LED, the subject S sensed by the 595 nm emission filter 60 is dyed with RFP, and the subject S sensed by the 690 nm emission filter 60 is dyed with Cy5.

As described above, according to the present invention, different images may be acquired through a plurality of emission filters 60 even though a single light source, a single focusing lens 20, a single excitation filter 30, and a single first dichroic mirror 40 are used, the configuration of the fluorescence imaging device may be simplified, and the manufacturing cost of the fluorescence imaging device may be reduced. Especially, the fluorescence imaging device may be very usefully used for distinguishing living cells and dead cells and counting the number of the cells so as to acquire information.

In addition, subjects S dyed with different fluorophores may be observed by moving only the emission filters 60 without moving the whole of a filter assembly (including a light source, a focusing lens, an excitation filter 30, a first dichroic mirror 40 (or a second dichroic mirror 41), and emission filters 60) as in the conventional fluorescence imaging device 1. Thus, the size and load of a moving part may be reduced and a change in alignment state of an optical path may be minimized.

Although specific exemplary embodiments of the present invention have been described and illustrated in the foregoing, it is obvious to a person ordinarily skilled in the art that the present invention is not limited to the described exemplary embodiments and may be variously changed and modified without departing from the idea and scope of the present invention. Accordingly, such changed examples or modified examples shall not be individually understood from the technical idea and viewpoint of the present invention and the modified or changed examples shall be deemed as belonging to the scope of the present invention defined by the claims.

What is claimed is:

1. A fluorescence imaging device comprising:
    a first light source which is a fluorescence light source;
    a second light source configured to irradiate a white light or a monochromatic light to a subject;
    an excitation filter configured to selectively transmit an excitation light irradiated by the first light source;
    a first dichroic mirror configured to transmit an excitation light transmitted by the excitation filter, to the subject and to reflect a fluorescent emission light emitted from the subject and a second light from the second light source;
    an objective lens configured to concentrate the fluorescent emission light reflected by the first dichroic mirror and the second light;
    an emission filter configured to transmit a light of a predetermined wavelength in the fluorescent emission light concentrated by the objective lens; and
    a detector configured to sense an image from the light that has transmitted through the emission filter and the second light.

2. The fluorescence imaging device of claim 1, wherein a plurality of emission filters are provided so as to transmit wavelengths of different regions, respectively, and selectively arranged on a path of the fluorescent emission light.

3. The fluorescence imaging device of claim 2, wherein the plurality of emission filters have different thicknesses.

4. The fluorescence imaging device of claim 3, further comprising:
    a filter wheel to which the plurality of emission filters are coupled,
    wherein the filter wheel arranges each of the emission filters on the path of the fluorescent emission light while rotating about a rotation shaft.

5. The fluorescence imaging device of claim 2, wherein the plurality of emission filters are positioned and moved on the same plane.

6. The fluorescence imaging device of claim 2, wherein a plane formed by the plurality of emission filters is orthogonal to the path of the fluorescent emission light.

7. A fluorescence imaging device comprising:
    a first light source which is a fluorescence light source;
    an excitation filter configured to selectively transmit an excitation light irradiated by the first light source;
    a first dichroic mirror positioned between an objective lens and a subject, the first dichroic mirror being configured to transmit an excitation light transmitted by the excitation filter to the subject and to reflect a fluorescent emission light emitted from the subject;
    an objective lens configured to concentrate the fluorescent emission light reflected by the first dichroic mirror;
    an emission filter configured to transmit a light of a predetermined wavelength in the fluorescent emission light concentrated by the objective lens; and
    a detector configured to sense an image from the fluorescent emission light transmitted by the emission filter.

8. The fluorescence imaging device of claim 7, wherein a plurality of first light sources, excitation filters and first dichroic mirrors are provided to be classified according to wavelengths.

9. A fluorescence imaging device comprising:
    a first light source which is a fluorescence light source;
    an excitation filter configured to selectively transmit an excitation light irradiated by the first light source;
    a second dichroic mirror positioned between an objective lens and a subject, the second dichroic mirror being configured to reflect an excitation light transmitted by the excitation filter to the subject and to transmit a fluorescent emission light emitted from the subject;
    an objective lens configured to concentrate the fluorescent emission light transmitted by the second dichroic mirror;
    an emission filter configured to transmit a light of a predetermined wavelength in the fluorescent emission light concentrated by the objective lens; and
    a detector configured to sense an image from the fluorescent emission light transmitted by the emission filter,
    wherein a plurality of first light sources, excitation filters and second dichroic mirrors are provided to be classified according to wavelengths.

* * * * *